United States Patent [19]

Shipp, Jr.

[11] 4,075,680

[45] Feb. 21, 1978

[54] CAPACITANCE DENSITOMETER FOR FLOW REGIME IDENTIFICATION

[75] Inventor: Roy L. Shipp, Jr., Oak Ridge, Tenn.

[73] Assignee: The United States of America as represented by the United States Department of Energy, Washington, D.C.

[21] Appl. No.: 763,435

[22] Filed: Jan. 27, 1977

[51] Int. Cl.² ............................................. H01G 7/00
[52] U.S. Cl. ................................. 361/285; 324/61 P; 361/278; 361/303
[58] Field of Search ............... 361/278, 303, 285, 329; 324/61 P

[56] References Cited

U.S. PATENT DOCUMENTS 3,176,222  3/1965  Atkisson .......................... 361/285 X Primary Examiner—E. A. Goldberg
Attorney, Agent, or Firm—Dean E. Carlson; Stephen D. Hamel; Louis M. Deckelmann

[57] ABSTRACT

This invention relates to a capacitance densitometer for determining the flow regime of a two-phase flow system. A two-element capacitance densitometer is used in conjunction with a conventional single-beam gamma densitometer to unambiguously identify the prevailing flow regime and the average density of a flowing fluid.

2 Claims, 2 Drawing Figures

CAPACITANCE DENSITOMETER FOR FLOW REGIME IDENTIFICATION

BACKGROUND OF THE INVENTION

This invention was made in the course of, or under, a contract with the U.S. Energy Research and Development Administration.

Two-phase flow studies are being conducted at the Oak Ridge National Laboratory in support of the Blowdown Heat Transfer Program. One subobjective in this program is to determine which of many possible flow regimes prevail in a water-stream mixture in the piping of the Thermal Hydraulic Text Facility and the determination of the average density of that mixture.

Single-beam gamma densitometers are very reliable devices that provide a good measurement of the density through that portion of the flow passing through the beam path. However, a knowledge of the flow regime is a prerequisite to obtaining the average density from single beam gamma densitometer data. In order to obtain flow regime information, a multiple-beam gamma densitometer or other flow regime diagnostic system is necessary. A multiple-beam gamma densitometer will give the essential information but requires large, heavy radiation shields and is relatively expensive.

Capacitance densitometry of the water-stream mixture appears to be useful for some flow regimes. In theory, multiple capacitor probes can be built that permit differentiation between horizontal stratified flow, annular flow, slug flow, and homogeneous flow regimes. The major problem is that a much smaller density indication for water droplets in steam than for steam bubbles in water leads to an inability to distinguish between the steam bubble and water droplet regimes. Thus, there exists a need for an improved multiple capacitor densitometer probe and a method for providing unambiguous flow regime information while also providing the average density for a two-phase flow system utilizing the capacitor probe in conjunction with a gamma densitometer. The above need has been met in the present invention in a manner to be described hereinbelow.

SUMMARY OF THE INVENTION

It is the object of the present invention to provide an improved capacitor densitometer probe that can be utilized in conjunction with a gamma densitometer to provide accurate flow regime information, while at the same time providing the average density for a two-phase flow system.

The above object has been accomplished in the present invention by providing a capacitor densitometer probe comprising a triangular-shaped capacitor plate and a rectangular shaped capacitor plate mounted in mating slots on opposite sides of electrical insulators and a pair of respective grounded capacitor plates mounted in spaced relation with respective ones of said other capacitor plates, and utilizing the capacitor probe in conjunction with a single-beam gamma densitometer to provide the flow regime information and average density in a unique manner as will be described hereinbelow.

DESCRIPTION OF THE PREFERRED EMBODIMENT

Figure 1:
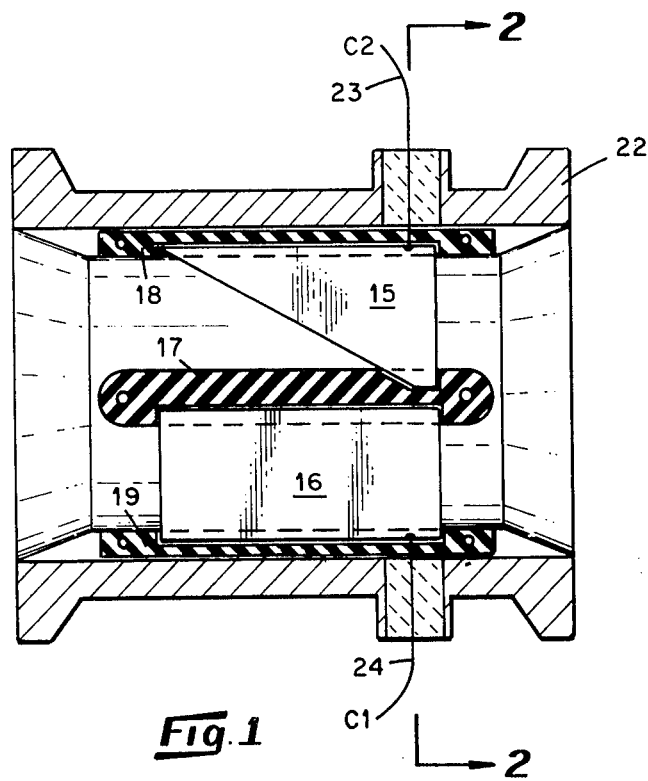
FIG. 1 is a cross-sectional view of the capacitor densitometer probe of the present invention.
Figure 2:
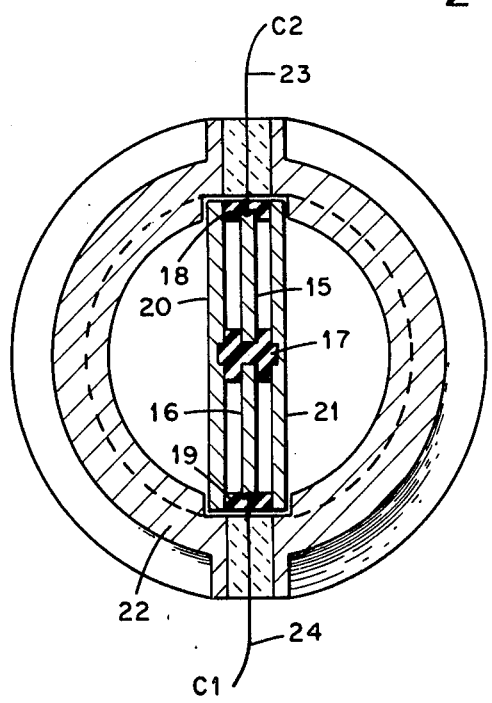
FIG. 2 is a cross-sectional view of the probe along the line 2—2 of FIG. 1.

FIGS. 1 and 2 of the drawings illustrate two views of the improved capacitor densitometer probe of the present invention, wherein a triangular-shaped capacitor plate 15 and a rectangular-shaped capacitor plate 16 are inserted into mating slots on opposite sides of an electrical insulator 17. The opposite ends of the plates 15 and 16 are inserted into mating slots in two other electrical insulators 18 and 19, respectively. These parts are held in place between two grounded capacitor plates 20 and 21 by means of rivets through the insulators 17, 18 and 19. It should be understood that the plates 20 and 21 may be constructed to conform to the general combined shapes of the plates 15 and 16, or any other desired shape such as to take care of any fringing effects. The plates 15 and 16, then, are the ungrounded electrodes of two separate capacitors C2 and C1, respectively. The plates 20 and 21 constitute the remainder of each capacitor defining its volume and therefore its value. This assembly is slid into two receiving grooves on the inside of a section of pipe 22 and spot welded into place. Electrical leads 23 and 24 that are attached to the ungrounded plates 15 and 16, respectively, are brought out through separate holes on opposite sides of the pipe 22.

The materials of construction for any given densitometer will depend on the application at hand. The capacitance densitometer constructed for the room temperature water-air mixture in the two-phase flow tests utilizes stainless steel for the metal parts and the insulators are fabricated from nylon. Nonorganic insulators will be required for use at temperatures of 550° to 650° F in the Blowdown Heat Transfer tests. In applications where water conductivity is high, it will be necessary to insulate the nongrounded electrodes from the water. The use of anodized aluminum or oxidized zirconium for the insulated plates would be practical, for example.

The electrodes will perturb the flow of the fluid in the densitometer. For the device to be useful, the pertubation must not adversely affect the operation of other nearby detectors. Also, the electrodes need to be able to withstand the dynamic forces of two-phase flow without flexing enough to materially alter the calibration of the densitometer.

In the operation of the above-described capacitance densitometer by itself, some flow regimes may be identified from the ratios of the two capacitor values. Generalizing from the theoretical data shown in the following Table 1, the flow regimes that can be determined are as follows:

Table 1

| | WATER-GAS MIXTURE AT ROOM TEMPERATURE AND PRESSURE | | | | |
|---|---|---|---|---|---|
| | Flow Regime | Void Fraction (%) | C1 (pf) | C2 (pf) | C1/C2 | Void fraction from Gamma Densitometer (% v.f.) |
| (a) | empty pipe | 100 | 10 | 5 | 2 | 100 |
| (b) | full pipe | 0 | 800 | 400 | 2 | 0 |
| (c) | annular flow | 50 | 234 | 200 | 1.17 | 70 |
| (d) | inverse annular | 50 | 571 | 200 | 2.85 | 30 |
| (e) | low density stratified | 66 | 690 | 5 | 137 | 100 |
| (f) | high density stratified | 33 | 800 | 36 | 22 | 0 |
| (g) | steam bubble | 50 | 320 | 160 | 2 | 50 |
| (h) | water droplet | 50 | 60 | 30 | 2 | 50 |

A C1/C2 ratio of 2 indicates the flow regime is either empty (a), full (b), or homogeneous flow (g), (h). The full and empty regimes may be determined directly from C1 or C2, but the inability to distinguish between the two homogeneous regimes through the capacitance ratio severely limits the usefulness of the capacitance densitometer by itself. A solution to this problem has been found and is described later.

A C1/C2 ratio of less than 2 indicates annular flow (c), i.e., water flowing in a ring at the pipe wall.

A C1/C2 ratio of greater than 2 indicates that the flow is either inverse annular (slug) (d) or stratified (e), (f). The low (e) and high (f) density stratified flow each have a distinguishing mark so that the absence of either of these marks indicates the flow is inverse annular or stratified low or high by the process of elimination. For low density stratified flow (e), C2 indicates empty and C1 has a midrange value. High density stratified flow (f) is indicated when C1 indicates full and C2 has a midrange value.

It should be understood that when the capacitance densitometer is monitoring fluid flows wherein the water thereof is less than pure, the readings obtained from the capacitors C1 and C2 will be a vector sum of the respective capacitances and the conductance between the capacitor plates, such that the C1 and C2 values of Table 1 but not C1/C2 may vary. Thus, the various flow regimes may still be determined in the same manner as described above.

By utilizing a single beam gamma densitometer in conjunction with the above-described capacitance densitometer, both the average densities and the flow regime determination can all be readily determined. The single beam gamma densitometer is a conventional system, wherein a source of gamma rays is positioned on one side of a flow pipe with the rays being directed through the pipe, and a receiver detector is positioned on the opposite side of the pipe from the gamma ray source for receiving the gamma rays attenuated by the fluid flowing through the pipe, wherein the output of the detector is an inverse function of the density of the flowing fluid.

When both the above densitometers are utilized, and again referring to Table 1, the following determinations can readily be made:

1. The flow regimes (a), (b) are identified as above. The gamma densitometer reads the average density.
2. The flow regime (c) is identified the same as above. The average density may be determined directly from C2 or calculated from the gamma density.
3. For inverse annular flow (d), the density reading from C1 and gamma should be in agreement. The average density can be determined directly from C2 or calculated from either C1 or gamma.
4. For low density stratified flow (e), C2 and gamma indicate empty and the average density is determined from C1.
5. For high density stratified flow (f), C1 and gamma indicate full pipe and the average density is calculated from $\frac{1}{2}$ full pipe plus a flow proportion indication from C2. In the practical capacitance densitometer, there is a dead region near the center that is occupied by the insulator between C1 and C2. During stratified flow it should be possible to measure in this region by the variation in gamma beam density.
6. The steam bubble (g) and water droplet (h) flow regimes may be differentiated by comparing gamma determined densities with capacitance determined densities. For both regimes, the gamma densitometer is reading average density. The gamma and capacitance densities will be in fair agreement for steam bubble flow, but the capacitance determined density will be much lower than the gamma density for water droplet flow.

This invention has been described by way of illustration rather than by limitation and it should be apparent that it is equally applicable in fields other than those described.

What is claimed is:

1. An improved two-element capacitance densitometer probe unit comprising a first insulator provided with slots on opposite sides thereof, a first triangular-shaped, ungrounded capacitor plate, a second rectangular-shaped, ungrounded capacitor one respective edge of each of said plates fitting within each of said respective slots of said insulator, a second insulator and a third insulator both provided with respective slots for receiving the other respective edges of said respective capacitor plates, a third capacitor plate and a fourth capacitor plate both adapted to be grounded, said third and fourth capacitor plates mounted on respective opposite sides of and in spaced relation to said first and second capacitor plates by means of all of said insulators and respective rivets therethrough, said probe unit adapted to be positioned into receiving grooves on the inside of a section of a flow tube and spot welded thereto, and a pair of respective output leads affixed to said respective first and second capacitor plates and adapted to extend exterior to said flow tube section through separate holes in opposite sides of said flow tube section, whereby the outputs of the respective capacitors formed by said capacitor plates can provide an indication of any one of several possible flow regimes existing in a flow tube in which said section containing said probe is mounted during the monitoring of two-phase flow through said flow tube.

2. The probe unit set forth in claim 1, wherein said insulators are nylon and said capacitance plates are stainless steel.

* * * * *

UNITED STATES PATENT OFFICE
CERTIFICATE OF CORRECTION

Patent No. 4,075,680    Dated February 21, 1978

Inventor(s) Roy L. Shipp, Jr.

It is certified that error appears in the above-identified patent and that said Letters Patent are hereby corrected as shown below:

Column 4, line 31, for "capacitor one" read ---capacitor plate, one---

Signed and Sealed this

Seventeenth Day of October 1978

[SEAL]

Attest:

RUTH C. MASON
Attesting Officer

DONALD W. BANNER
Commissioner of Patents and Trademarks